US00PP26578P2

(12) United States Plant Patent
van Oploo

(10) Patent No.: US PP26,578 P2
(45) Date of Patent: Apr. 5, 2016

(54) ***PHOTINIA* PLANT NAMED 'OPLOO5'**

(50) Latin Name: *Photinia serratifolia*
Varietal Denomination: Oploo5

(71) Applicant: Alexander A. A. M. van Oploo, Bavel (NL)

(72) Inventor: Alexander A. A. M. van Oploo, Bavel (NL)

( * ) Notice: Subject to any disclaimer, the term of this patent is extended or adjusted under 35 U.S.C. 154(b) by 142 days.

(21) Appl. No.: 14/120,057

(22) Filed: Apr. 21, 2014

(51) Int. Cl.
*A01H 5/12* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Penny J. Aguirre

(57) ABSTRACT

A new cultivar of *Photinia*, 'Oploo5', that is characterized by its bushy, loose, broad spreading, and upright plant habit, its young leaves that are grayed-red to grayed-orange in color and heavily marbled with yellow-green in unique patterns on all leaves, and its mature leaves that are marbled in various patterns with grayed-green, green and yellow-green.

3 Drawing Sheets

Botanical classification: *Photinia serratifolia.*
Variety denomination: 'Oploo5'.

BACKGROUND OF THE INVENTION

The present invention relates to a new and distinct cultivar of *Photinia serratifolia*, and will be referred to hereafter by its cultivar name, 'Oploo5'. 'Oploo5' is a new cultivar of evergreen shrub grown for use as a landscape plant.

The Inventor discovered the new cultivar in June of 2002 as a naturally occurring branch mutation of *Photinia* 'Jenny' (not patented) in a production container block at the Inventor's nursery in Bavel, The Netherlands.

Asexual reproduction of the new cultivar was first accomplished by softwood stem cuttings by the Inventor in Bavel, The Netherlands in 2010. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Oploo5' as unique cultivar of *Photinia.*

1. 'Oploo5' exhibits a bushy, loose, broad spreading, upright plant habit.
2. 'Oploo5' exhibits young leaves that are grayed-red to grayed-orange in color and heavily marbled with yellow-green in unique patterns on all leaves.
3. 'Oploo5' exhibits mature leaves that are marbled in various patterns with grayed-green, green and yellow-green.

'Jenny', the parent of 'Oploo5', differs from 'Oploo5' in having leaves that are solid green and not variegated. There are no cultivars of *Photinia serratifolia* with variegated foliage known to the Inventor. 'Oploo5' can also be compared to the *Photinia×fraseri* cultivars 'Indian Summer' (not patented) and 'Cassini' (U.S. Plant Pat. No. 15,160). 'Indian Summer' is similar to 'Oploo5' in having new growth that is orange in color, but differs from 'Oploo5' in having foliage that is non-variegated. 'Cassini' is similar to 'Oploo5' in having variegated leaves. 'Cassini' differs from 'Oploo5' in having longer internodes, in having young leaves that are bright red and pink in color, and in having mature leaves that have green centers and white margins.

BRIEF DESCRIPTION OF THE DRAWINGS

The accompanying colored photographs illustrat the overall appearance and distinct characteristics of 3 year-old plants of the new *Photinia* as field grown outdoors in Bavel, The Netherlands.

The photograph is FIG. 1 provides a side view of the overall plant habit of 'Oploo5'.

Figure 1:
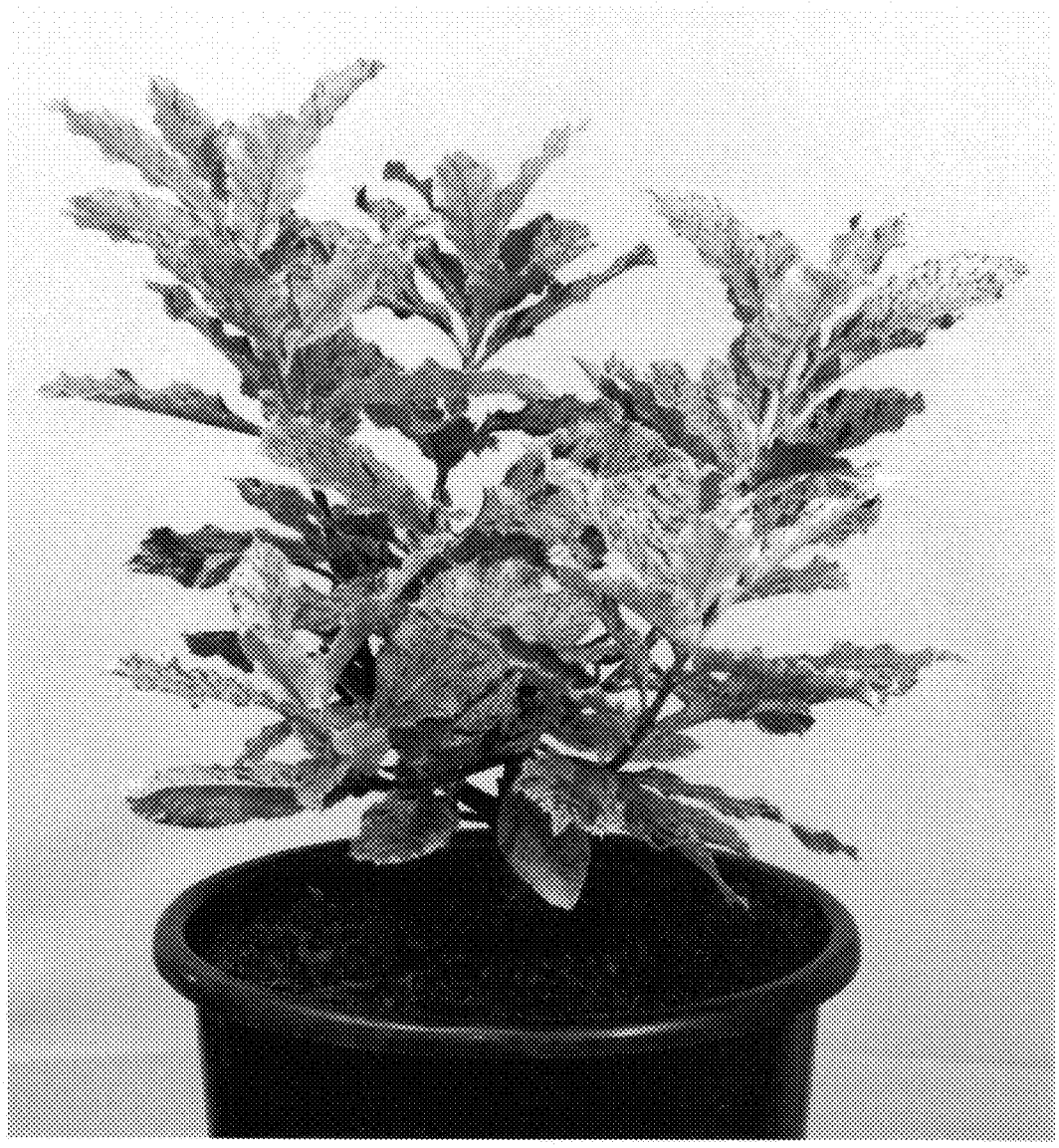
Figure 2:
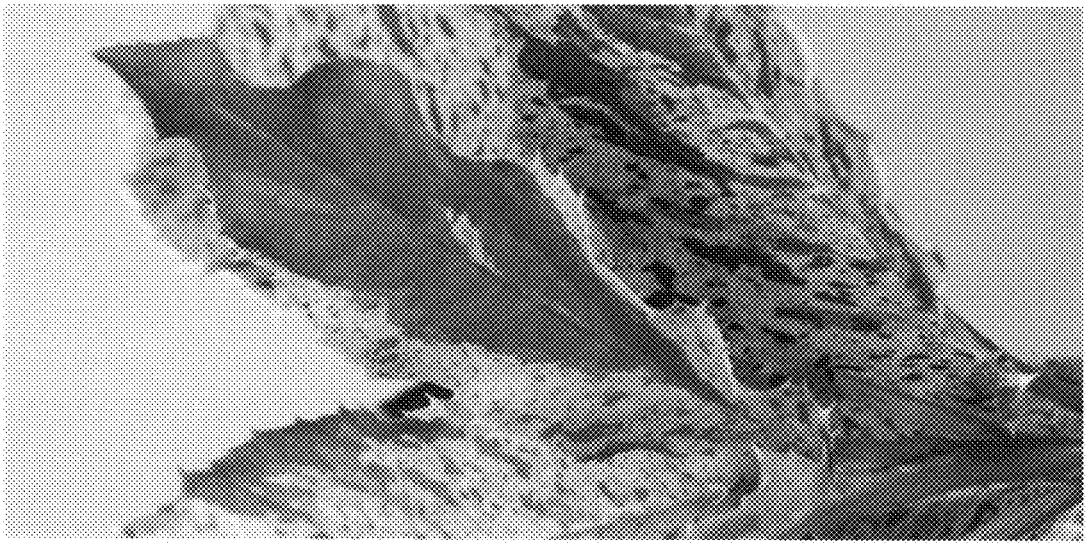
Figure 3:
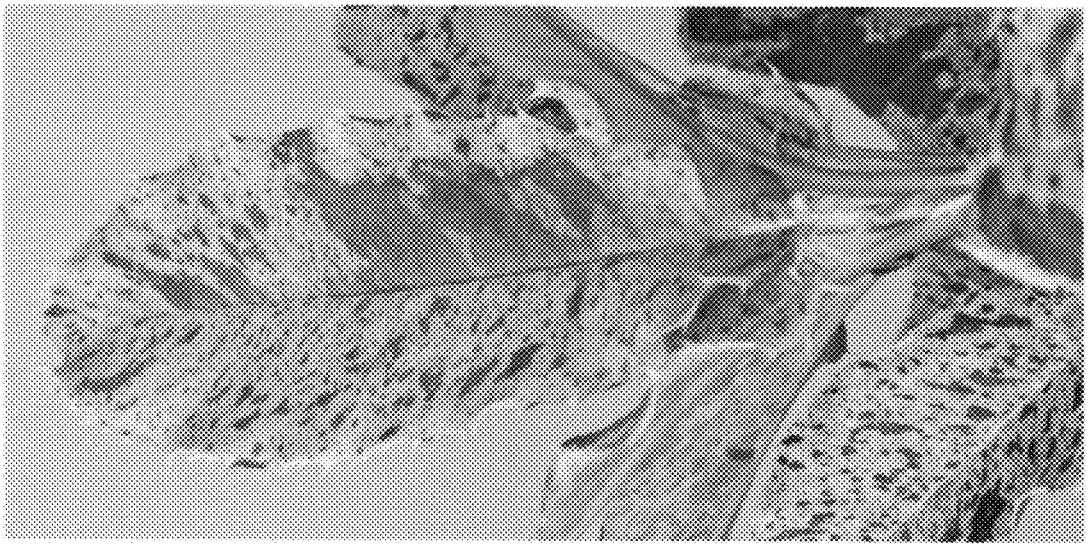

The photographs in FIG. 2 and FIG. 3 provide close-up views of the young foliage of 'Oploo5'.

Figure 4:
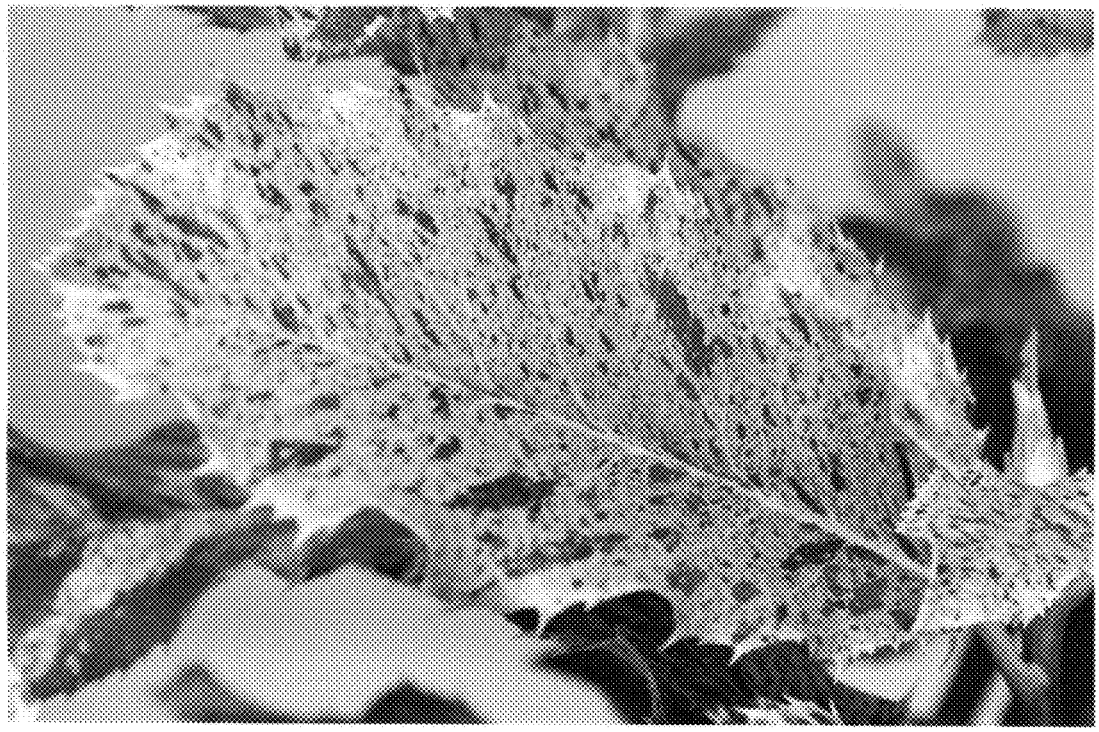
Figure 5:
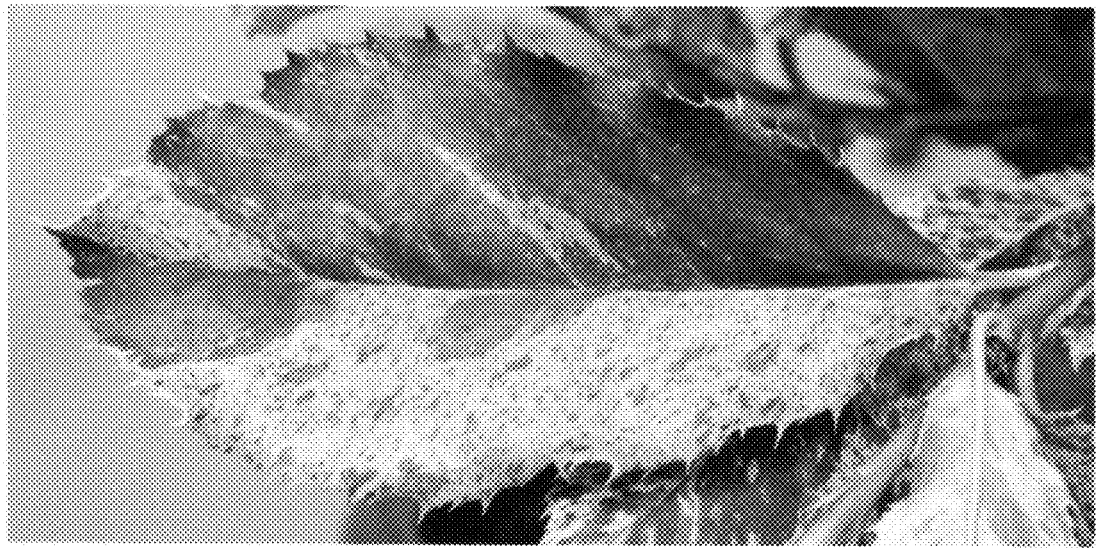

The photographs in FIG. 4 and FIG. 5 provide close-up views of mature foliage illustrating the variation in marbling of leaves of 'Oploo5'.

The colors in the photographs are as close as possible with the digital photography techniques available and the color values cited in the detailed botanical description most accurately describe the colors of the new *Photinia.*

DETAILED BOTANICAL DESCRIPTION

The following is a detailed description of 3 year-old plants of the new *Photinia* as field grown in Bavel, The Netherlands (and placed in a container for the photographs). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen, perennial bushy shrub.

*Plant habit*.—Bushy, loose, broad spreading, upright plant habit.

*Height and spread*.—An average of 42.2 cm in height and 54.9 cm width as a 3 year-old plant and reaches up to 150 cm in height and 100 cm in width as a mature plant in the landscape.

*Cold hardiness*.—At least to U.S.D.A. Zone 7b.

*Diseases and pests*.—No susceptibility or resistance to diseases or pests has been observed.

*Root description*.—Fibrous.

*Root development*.—Roots initiate in about 8 weeks, a rooted cutting will fully develop in a 10-cm container in about 16 weeks.

*Propagation*.—Stem cuttings.

*Growth rate*.—Moderate to high.

Stem description:

*Shape*.—Rounded.

*Stem color*.—New twigs; 144A suffused with 174B, mature bark; 200D with lenticels 199C in color.

*Stem size*.—Lateral branches average 17.5 cm in length and an average of 5 mm in diameter.

*Stem surface*.—Smooth, glabrous, glossy, lenticellate.

*Branching*.—Moderately freely branched, an average of 6 lateral branches.

*Branch internode length*.—Average of 2.2 cm.

Foliage description:

*Leaf shape*.—Obovate.

*Leaf division*.—Simple.

*Leaf base*.—Attenuate.

*Leaf apex*.—Apiculate to abruptly acute, typically twisted.

*Leaf fragrance*.—None.

*Leaf venation*.—Pinnate, color; identical to leaf.

*Leaf margins*.—Strongly serrate and strongly wavy.

*Leaf arrangement*.—Alternate.

*Leaf attachment*.—Petiolate.

*Leaf number*.—Average of 9 per lateral branch.

*Leaf surface*.—Upper and lower surface; smooth, glabrous and moderately glossy.

*Leaf size*.—Average of 12.8 cm in length and 6.4 cm in width.

*Leaf color*.—Newly expanded leaves upper surface; a blend between 179C and 174C to 174D and heavily marbled with a blend between 146A and 148A, newly expanded leaves lower surface; 182D and slightly marbled and suffused with a blend of 146D and 148D, mature leaves upper surface; a blend of 192A, 192C, and 194B and heavily marbled with a blend of N137A, 147A, and N189B, mature leaves lower surface; a blend of 193B and 194B to 194D.

*Petioles*.—Average of 1.1 cm in length and 3 mm in width, color; 144C suffused with 180D in older leaves, surface is glabrous and glossy.

*Stipules*.—2, present on each side of the petiole, narrow deltoid in shape, an average of 6 mm in length and 3 mm in width, 146D with margins 147D in color, leafy in substance, glossy on both surfaces.

Flower description: The new cultivar has not produced flowers.

It is claimed:

1. A new and distinct cultivar of *Photinia* plant named 'Oploo5', as herein illustrated and described.

* * * * *